United States Patent
Saab

[11] Patent Number: 6,004,289
[45] Date of Patent: *Dec. 21, 1999

[54] MULTIPLE LAYER HIGH STRENGTH BALLOON FOR DILATATION CATHETER

[75] Inventor: Mark A. Saab, Lawrence, Mass.

[73] Assignee: Medtronic AVE, Inc., Santa Rosa, Calif.

[*] Notice: This patent is subject to a terminal disclaimer.

[21] Appl. No.: 08/827,228

[22] Filed: Mar. 28, 1997

Related U.S. Application Data

[63] Continuation of application No. 08/327,300, Oct. 21, 1994, Pat. No. 5,775,690, which is a continuation of application No. 07/928,135, Aug. 11, 1992, Pat. No. 5,358,486, which is a continuation of application No. 07/523,490, May 15, 1990.

[51] Int. Cl.$^6$ .................................................. A61M 29/00
[52] U.S. Cl. ........................... 604/96; 606/194; 428/35.2; 156/245
[58] Field of Search ...................... 604/96–103; 264/454; 606/192–196; 128/207.15; 428/35.2; 156/244.13, 294.573, 245

[56] References Cited

U.S. PATENT DOCUMENTS

| | | |
|---|---|---|
| 4,490,421 | 12/1984 | Levy . |
| 4,994,033 | 2/1991 | Shockey et al. . |
| 5,358,486 | 10/1994 | Saab . |
| 5,755,690 | 5/1998 | Saab . |

FOREIGN PATENT DOCUMENTS

23 733/77   3/1977   Australia .

*Primary Examiner*—Mark Bockelman
*Attorney, Agent, or Firm*—Sterne, Kessler, Goldstein & Fox P.L.L.C.

[57] ABSTRACT

A multilayer high strength balloon for a dilatation catheter is provided. The balloon comprises a plurality of balloon layers, including an inner layer which has a cylindrical midportion, a cone at each end, and necks at the ends of the cones, and at least one additional layer which has the cylindrical midportion and cones. Each layer is formed from a polymeric material, and perhaps an inelastic, biaxially oriented, thermoplastic material. Preferably, one or more of the balloon layers is blow molded and stretched to biaxially orient the material to form a very high strength layer. The layers have differing lengths along the catheter to which the multilayer balloon is coupled. The multilayer balloon resulting from the plurality of balloon layers, of which one or more has been biaxially oriented, is stronger than a single layer balloon of the same finished diameter which has been made from the same material with comparable thickness. The composite high strength balloon may be formed to eliminate undesirable thickening of the cone regions of conventional blow molded balloon designs by stepping the cone regions so that they are not substantially greater than the wall thickness in the midportion of the balloon. The resulting balloon is better adapted to collapse to a low profile about the catheter shaft on which it is mounted.

20 Claims, 4 Drawing Sheets

MULTIPLE LAYER HIGH STRENGTH BALLOON FOR DILATATION CATHETER

This is a continuation, of application Ser. No. 08/327,300, filed Oct. 21, 1994 now U.S. Pat. No. 5,755,690, which is a continuation of Ser. No. 07/928,135, filed Aug. 11, 1992 now U.S. Pat. No. 5,358,486, which is a continuation of Ser. No. 07/523,490, filed May 15, 1990 now abandoned.

FIELD OF THE INVENTION

This invention relates to balloons used in dilatation catheters and to methods for making such balloons.

BACKGROUND OF THE INVENTION

Balloon dilatation catheters are used in the treatment of a variety of vascular conditions. Among the more frequent uses for balloon dilatation catheters is in vascular angioplasty of the peripheral and coronary arteries, by which arteries obstructed by plaque (formed by fatty deposits such as cholesterol) are dilated to improve blood flow through the artery. In a typical angioplasty procedure, a balloon dilatation catheter is inserted percutaneously into the patient's arterial system and then is advanced and steered through the patient's arteries until the distal end of the catheter, that carries the balloon, is disposed adjacent the obstruction (stenosis). The balloon end of the catheter then is advanced into the stenosis and, when so placed, is inflated under high pressure, to dilate the artery in the region of stenosis. The catheter typically is used with a small diameter steerable guidewire which is used to guide the catheter to the stenosis. By way of example, such a catheter and guidewire system is disclosed in U.S. Pat. 4,545,390 issued Oct. 8, 1985 (Leary), reference thereto being made for a more complete description of the catheter and guidewire system and its manner of use.

It is desirable, particularly in coronary angioplasty in which the coronary arteries are narrow and tortuous, and in which the stenoses often may be calcified and difficult to dilate, that the catheter and its balloon meet a number of stringent requirements. Among these are that the balloon be capable of folding down to a low profile about the catheter shaft so that the balloon portion of the catheter is more readily insertable through the stenosis. Inability to insert the balloon portion of the catheter into the stenosis is among the more frequent causes of an unsuccessful angioplasty. Also among the important characteristics of the balloon dilatation catheter is that it should be "trackable", that is, it must be able to follow and advance over the guidewire and through the artery even when the artery is highly tortuous with many sharp bends. An additional important characteristic of the balloon is that it should have a high burst strength so that it may dilate hard, calcified stenoses as well as those that require less force for the dilation.

In order to improve the low profile and trackability characteristics of the character in the region of the balloon, efforts have been made to develop dilatation balloons having very thin walls so that the balloon will fold more readily to a low profile about the catheter shaft and also so that the balloon will be more flexible, thus enhancing the ability of the catheter to bend in the region of the balloon, thereby achieving improved trackability. To that end, significant advances have been made in the art. U.S. Pat. 4,490,421 describes the manufacture of dilatation balloons by which balloons may be made having a high burst strength and significantly thinner walls than its predecessors. The procedure was improved further, as described in prior co-pending U.S. patent application Ser. No. 001,759, filed Jan. 9, 1987, now abandoned and the complete application being explicitly incorporated herein, to enable the manufacture of high strength balloons having even thinner, more flexible walls.

Although the foregoing advances in manufacturing thinner walled balloons have significantly improved the catheters, those efforts have been directed at the cylindrical midportion of the balloon. The cones and necks of the balloon, at the ends of the cylindrical midportion, are not as thin as the cylindrical midportion. Each cone is of increasing wall thickness in a direction away from the cylindrical midportion of the balloon and reaches a maximum wall thickness at its juncture with the necks. The wall thickness of the neck is at that maximum value throughout their length. The increased wall thickness of the balloon in the regions of the cones and the necks detracts from the ability of the balloon to collapse to a low profile as well as the ability of the balloon to track along the guidewire along sharp tortuous paths. It would be desirable, therefore, to provide a balloon for a dilatation catheter in which the wall thickness in the cone and neck portions is reduced and, preferably, is not substantially greater than the thickness in the cylindrical midportion of the balloon. It is among the objects of the invention to provide such a balloon and method for its manufacture.

It is among the general objects of the invention to provide improved dilatation balloons and a method for their manufacture which provides superior properties of thin walls, flexibility and high strength as well as full dimensional stability both in storage and when inflated.

SUMMARY OF THE INVENTION

The balloon of the present invention is formed from a plurality of thin layers rather than from a single unitary layer, the aggregate wall thickness of the layers being approximately equal to the wall thickness of a conventional single layer balloon in the cylindrical midportion. The balloons are made by blow molding a first balloon in a cylindrical mold from a thin walled polymeric tubular parison, as described in U.S. patent application Ser. No. 001,759, filed Jan. 9, 1987.

In accordance with the invention, the balloon is formed from a tubular wall parison of orientable semicrystalline polymer (polyethylene terephthalate being preferred) which is stretched very close to the elastic limit of the material and is then heat set. The balloon thus produced is extremely strong and has a very thin and highly flexible wall and is dimensionally stable both in storage and when inflated. Thus, it is among the objects of the invention to provide dilatation balloons having superior properties of thin walls, high tensile strength and dimensional stability. More specifically, it is among the objects of the invention to provide dilatation balloons having radial tensile strength (hoop strength) greater than 35,000 psi. The balloon then is removed from the mold and is trimmed at its ends to remove the necks and a portion of the cones. The trimmed balloon then is replaced in the mold against the mold walls. A second polymeric tube then is inserted into the mold and it is blow molded, expanding outwardly against the confines of the cylindrical mold and the inner surface of the first trimmed balloon. Then the combined first and second balloons are removed from the mold and the second balloon is trimmed at its ends to be slightly longer than the first trimmed balloon. The combined first and second balloons then are replaced in the mold and the process is repeated, inserting a tubular polymeric parison in the mold and blow molding it to expand into engagement with the second trimmed balloon. The combined first, second and third balloons then are removed from the mold, the ends of the third tube may be trimmed to leave the necks on the third, innermost balloon. The resulting balloon thus has cones in which the wall thickness does not increase substantially and in which the wall thickness in the neck region also is substantially less than with prior techniques for making such balloons. The resulting balloon is more flexible in the cone and neck region than with prior balloons.

It is among the objects of the invention to provide a balloon for a dilatation catheter and a method for making the balloon.

Another object of the invention is to provide a balloon dilatation catheter having improved low profile and trackable characteristics in the region of its cones and necks.

Another object of the invention is to provide a dilatation balloon construction in which the cone and neck regions are not substantially greater in wall thickness than the cylindrical midportion of the balloon.

A further object of the invention is to provide a balloon for a dilatation catheter in which the balloon is formed from a plurality of thin layers in intimate contact with each other.

It is also among the objects of the invention to provide dilatation balloons and dilatation catheters having low profiles with superior trackability and balloon foldability. Also among the objects of the invention is to provide a method for making such balloons. The invention thus provides for a method for making a family of such balloons which display the foregoing properties and which are usable in a variety of medical procedures.

BRIEF DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
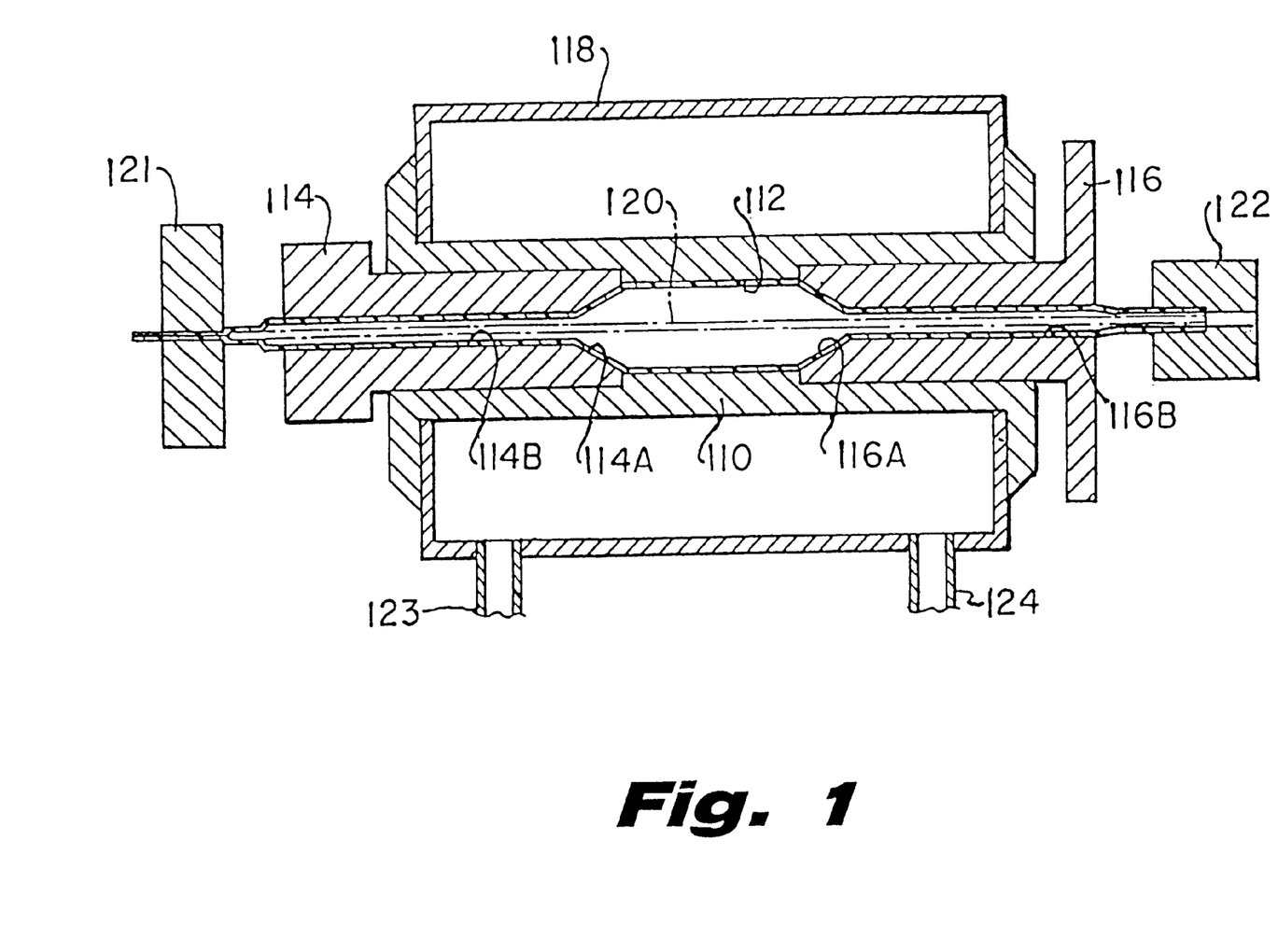
FIG. 1 is an illustration, in section, of a multi-part jacketed mold having the balloon formed within the mold and illustrating the tubular parison in phantom.

The balloon may be formed in a mold as illustrated in FIG. 1 which includes a mold body 110 having an internal bore which defines the intended dimension of the finished balloon, indicated at 112, and a pair of end members including a fixed end member 114 and a movable end member 116. Both end members include outwardly tapering portions 114A, 116A, respectively, which merge into smaller diameter end bores 114B, 116B, respectively. A water jacket 118 having inlet and outlet ports 123, 124 surrounds the mold 110. The mold parts are formed from a material, such as brass having good heat conductivity.

The mold receives a tubular parison, indicated in phantom at 120 in FIG. 1. The parison 120 is gripped at its ends which extends outwardly of the mold, one of the ends being sealed and the other end being connected securely to a source of fluid (such as a gas) under pressure as by a fitting 122. The clamp 121 and fitting 122 are mounted, by means not shown, to enable them to be drawn apart axially so as to impart an axial stretch to the parison 120.

The parison is formed from an orientable semicrystalline polymer such as polyethylene terephthalate (PET). In accordance with the invention, the parison is dimensioned with respect to the intended final configuration of the balloon. It is particularly important that the parison is relatively thin walled and that it is highly oriented being stretched radially close to the elastic limit of the material at the inner surface of the tube. The wall thickness is considered relative to the inside diameter of the parison tube. The present invention relates to thin walled parisons which have wall thickness-to-inside diameter ratios of less than 0.5 and, preferably between 0.45 and 0.09 or even lower. The use of such a thin walled parison enables the parison to be stretched radially to a greater and more uniform degree because there is less stress gradient through the wall from the surface of the inside diameter to the surface of the outside diameter. By utilizing thin wall starting parisons, there is less difference in the degree to which the inner and outer surfaces of the tubular parison are stretched. By maintaining a lower stretch gradient across the wall of the parison, it is possible to produce a more uniformly and more highly oriented balloon having tensile strengths substantially higher than those of the prior art.

Orientation takes place at an elevated temperature, as controlled by a heat transfer fluid, such as hot water, circulated through the water jacket. The PET parison preferably is drawn axially and while being so drawn, is expanded radially within the mold. The orientation takes place at a temperature between the first and second order transition temperatures of the material, preferably about 80° C.–99° C. and more preferably at about 90° C. The tube is drawn from a starting length L1 to a drawn length L2 which preferably is between 2.5 to 6 L1. The tubular parison, which has an initial internal diameter $ID_1$ and an outer diameter $OD_1$ is expanded by gas emitted under pressure to the parison through fitting 122 to an internal diameter $ID_2$ which preferably is 6 to 8 $ID_{s1}$ and an outer diameter $OD_2$ which is about equal to or preferably greater thar 4 $OD_1$. The expanded balloon then is subjected to a heat set step in which steam is circulated through the jacket 118 at a temperature above the stretching temperature and between 110° C. to 220° C. and preferably about 130°–170° C. and is maintained for a fraction of a second or more, and preferably between about 5 to 30 seconds sufficiently to increase the degree of crystallinity in the balloon. The heat setting step is significant in assuring dimensional stability for the balloon, both during storage and also under inflation pressures. After the heat set step, the mold is cooled to a temperature less than the second order transition temperature of the material. The balloon thus formed may be removed from the mold by removing the end piece 116 and withdrawing the formed balloon from the mold.

The degree of radial stretch in the resulting balloon is very close to the elastic limit of the material (at the inner surface) and, preferably is within 10% of the maximum achievable radial expansion for the material under the process conditions used. The high degree of orientation strengthens the balloon to tensile strengths of more than 35,000 psi and as high as 90,000 psi or more. For example, balloons made in accordance with the invention have a wall thickness to balloon diameter ratio (T/D) of the order of $5\times10^{-3}$ to $8\times10^{-5}$, with tensile strengths as high as 90,000 psi.

Table 1 below illustrates the T/D ratios for finished balloons of the present invention in comparison with T/D ratios for prior art balloons. Data for the balloons identified A–E was taken from Levy patent 4,490,421 for the correspondingly designated balloons in that patent.

$$S_c = \frac{PD}{2t}$$

where $S_C$ is the radial tensile strength, P is the burst pressure, D is the diameter of the balloon and t is the wall thickness. Wall thicknesses similarly were calculated and the thicknesses were cubed to provide an indication of relative stiffness.

Figure 2:
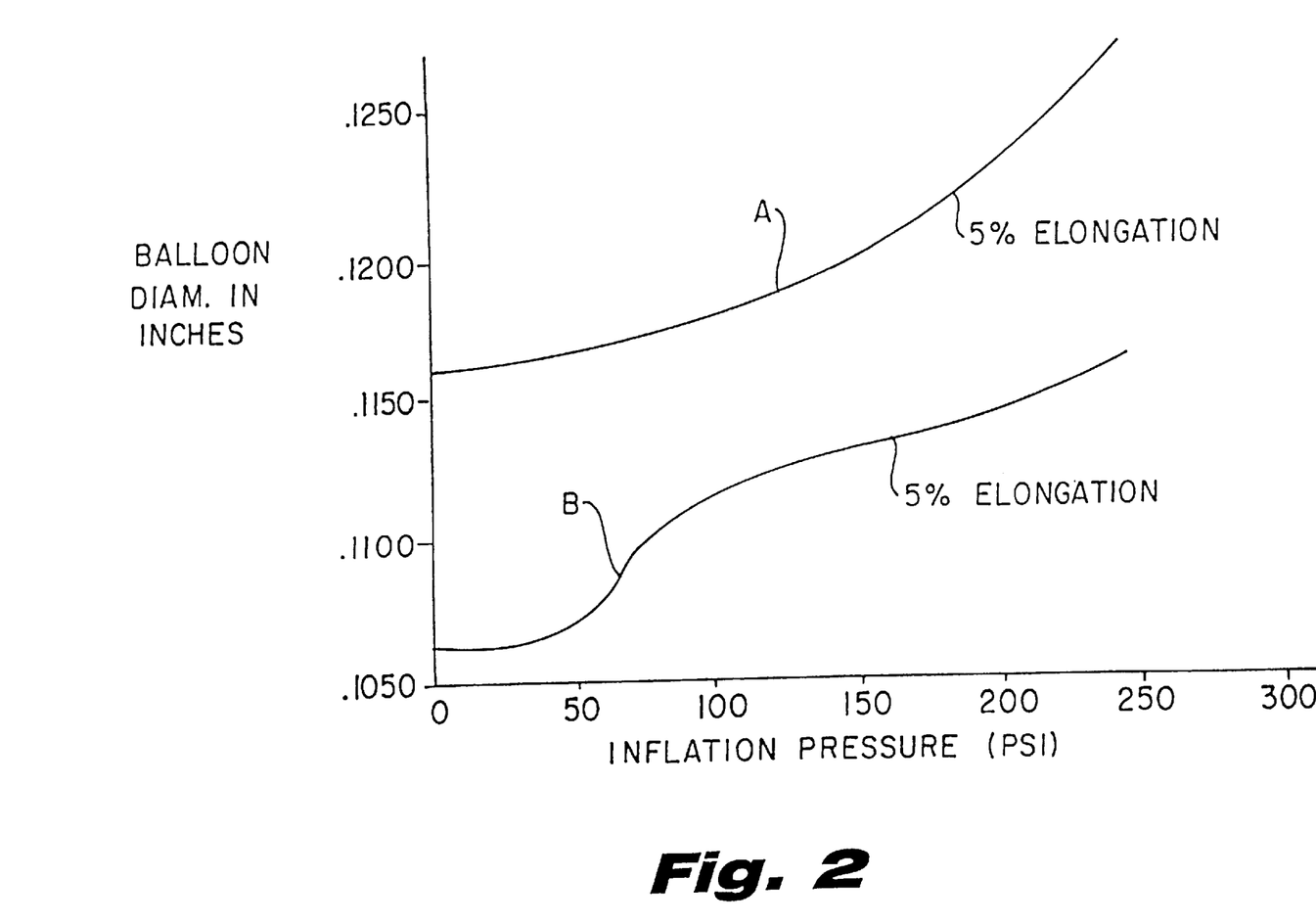
FIG. 2 shows the difference in dimensional stability between the balloon made in accordance with the invention in is which the balloon is heat set and a balloon which omits heat setting.

FIG. 2 shows the effect of the heat set step in the practice of the invention and compares the dimensional stability in storage as well as when inflated, of a balloon which has been heat set (curve A) to one which has not been heat set (curve B). Both balloons were formed in a cylindrical mold having a diameter 0.11711", under identical conditions of

TABLE 1

WALL THICKNESS (T)/BALLOON DIAMETER (D) RATIO

| | PRIOR ART | | | | | PRESENT INVENTION | | | |
|---|---|---|---|---|---|---|---|---|---|
| | A | B | C | D | E | F | G | H | I |
| T | .028 mm | .038 mm | .028 mm | .038 mm | .045 mm | .0136 mm | .0054 mm | .00806 mm | .0016 mm |
| D | 3.7 mm | 5.0 mm | 3.7 mm | 5.0 mm | 6.0 mm | 3.0 mm | 4.0 mm | 20.0 mm | 20.0 mm |
| T/D | $7.57 \times 10^{-3}$ | $7.6 \times 10^{-3}$ | $7.57 \times 10^{-3}$ | $7.6 \times 10^{-3}$ | $7.5 \times 10^{-3}$ | $4.5 \times 10^{-3}$ | $1.8 \times 10^{-3}$ | $4.03 \times 10^{-4}$ | $8.05 \times 10^{-5}$ |
| Burst at | | | | | | 352 psi | 220 psi | 73.5 psi | |

The balloons of the present invention display a remarkable increase in flexibility as compared to the prior PET balloons (Levy '421 patent). Flexibility is a function of the cube of the wall thickness, assuming all other variables, such as balloon material, balloon diameter, etc. are held constant. Table 2 illustrates the effect on flexibility of the thinner balloons of the present invention as compared with those of the prior art.

temperature, time and pressure except that the heat set balloon was subjected to the heat set procedure as described above. The other balloon was cooled following the radial expansion, without any heat set. The balloons were removed from their molds and were permitted to remain in ambient conditions (20° C.) for 48 hours. The balloons then were tested by inflating them under increasing pressures and measuring the balloon diameter as the pressure was

TABLE 2

| | PRIOR ART (LEVY) | | | SAAB DISCLOSURE | | | Improvement in Flexibility Over Prior Art (%) |
|---|---|---|---|---|---|---|---|
| Burst Pressure (Bars) | Radial Tensile Strength (psi) | Wall Thickness (mils) | Relative Stiffness ($T^3$) | Radial Tensile Strength (psi) | Wall Thickness (mils) | Relative Stiffness ($t^3$) | $\left[\frac{(t^3 - T^3)}{T^3}\right] \times 100)$ |
| 5 | 34,000 | 0.13 | 0.0022 | 90,000 | 0.048 | 0.00011 | 1,900 |
| 10 | 34,000 | 0.25 | 0.016 | 75,000 | 0.114 | 0.0015 | 1,000 |
| 15 | 34,000 | 0.38 | 0.054 | 65,000 | 0.20 | 0.0077 | 600 |
| 20 | 34,000 | 0.50 | 0.127 | 52,000 | 0.33 | 0.036 | 250 |
| 25 | 34,000 | 0.63 | 0.249 | 40,000 | 0.53 | 0.15 | 65 |

From Table 2 it can be seen that for balloons having burst pressures up to about 25 bars, the relative stiffness of the balloons of the present invention is far less than that of the prior art PET balloons. The flexibility of the balloons of the present invention, considered as a function of the cube of the thickness ($t^3$) of the balloons far exceeds those of the prior art. In the data presented in Table 2, the radial tensile strength was calculated at burst pressure. Wall thicknesses were calculated using the well known pressure vessel equation increased. As shown in FIG. 2, the heat set balloon, when nominally inflated to remove wrinkles (about 10 psi) had a diameter of about 0.116", reflecting a shrinkage of 0.001". By contrast, the non-heat sealed balloon showed a nominal diameter of 0.1060, indicating a very substantial diametral shrinkage of 0.011". As the pressure was increased, the heat set balloon showed relatively steady and slow yielding, reaching 5% radial expansion at about 170 psi. In contrast, the non-heat set balloon displayed very substantially yielding and radial expansion in the range of 50 to 100 psi, reaching 5% radial expansion at about 85 psi.

The superior properties of balloons made in accordance with the invention may be appreciated further from the "F5" characteristics of the balloon. In oriented polymers the tensile strength at 50% elongation is referred to as "F5". FIG. 2 illustrates, on curve A, the point on which a balloon made in accordance with the invention has achieved 5% radial expansion. In curve A the F5 point occurs at about 170 psi inflation pressure. The balloon reflected in curve A is the balloon identified as balloon G in Table 1 (and in Example 2 below), having a wall thickness of 0.0054 mm and a diameter of 3.0 mm. From the pressure vessel equation, the radial tensile strength at 5% radial expansion is calculated to be 47,600 psi. That is contrasted with the prior art (Levy '421) balloons in which the maximum tensile strength achievable to burst is of the order of 34,000 psi. Thus, the present invention provides for F5 radial tensile strengths greater than 30,000 psi.

The following examples illustrate several balloons which may be made in the range of balloons achievable in accordance with the present invention.

EXAMPLE 1

A tubular parison was extruded from high molecular weight PET homopolyester resin having an initial intrinsic viscosity of about 1.04. The parison had an inner diameter of 0.429 mm, an outer diameter of 0.789 mm, a wall thickness of 0.180 for a wall thickness-to-ID ratio of 0.42. The parison was stretched axially 3X, was stretched 7X ID and 3.8X OD to form a 3.0 mm balloon having a wall thickness of 0.0136 mm. The balloon was heat set. The balloon had a burst pressure of 24 bars (23.7 atm) and a calculated radial tensile strength of about 38,900 psi. This balloon corresponds to the balloon designated "F" in Table 1.

EXAMPLE 2

A parison was formed in the manner described above in Example 1 to have an inner diameter of 0.429 mm and an outer diameter of 0.638 mm, having a parison wall thickness/ID ratio of 0.25. The parison was stretched axially 3.3X, was stretched 7X ID and 4.7X OD to produce a heat set 3.0 mm balloon having a wall thickness of 0.0054 mm measured burst strength of 15 bars (14.8 atm) and a calculated radial tensile strength of about 61,250 psi. This balloon corresponds to balloon G in Table 1.

EXAMPLE 3

A parison was formed in the manner described about in Example 1 to have an ID of 2.86 mm and an OD of 3.39 mm, with a wall thickness/ID ratio of 0.09. The parison was stretched at 90° C. in an axial direction 3.75X and radially 7X ID and 5.9X OD to produce a heat set 20 mm balloon having a wall thickness of 0.00806, a measured burst strength of 5 bars (4.9 atm) and calculated radial tensile strength of 91.200 psi. This balloon corresponds to balloon H in Table 1.

It should be understood that the foregoing description of the invention is intended merely to be illustrative and that other embodiments and modifications may be apparent to those skilled in the art without departing from its spirit.

For example, the preferred aromatic linear polyester described for making balloons in accordance with the invention is polyethylene terephthalate derived from an aromatic dicarboxylic acid or its derivatives as a main acid component and an aliphatic glycol as a main glycol component. This polyester is a melt extrudable orientable semicrystalline polymer that can be fabricated into a variety of formed structures. Typical examples of other aromatic dicarboxylic acid polymers that meet these criteria utilize materials such as terepthalic acid, isothalic acid, naphthalene dicarboxylic acid, together with aliphatic polyethylene glycols having two to ten carbon atoms. Among these are ethylene glycol, trimethylene glycol, tetramethylene glycol, pentamethylene glycol, hexamethylene glycol, didecamethylene glycol and cyclohexane dimethanol.

Figure 3:
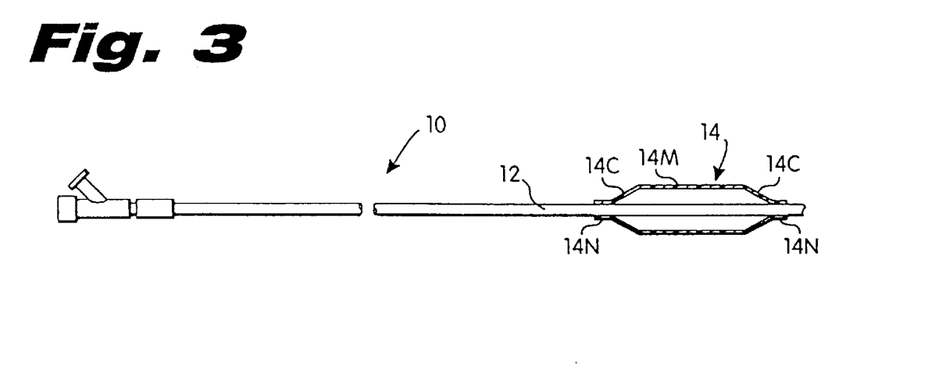
FIG. 3 is an illustration of a balloon dilatation catheter.

FIG. 3 illustrates a balloon dilatation catheter of the type with which the present invention is concerned. The catheter 10 has a proximal end (to the left in FIG. 3) and a distal end (to the right in FIG. 3). An elongate flexible shaft 12 typically is provided with appropriate lumens, for example, a guidewire lumen (not shown) that extends the length of the shaft and an inflation lumen (not shown) that extends from the proximal end of the shaft to the distal region of the shaft and communicates with the interior of a dilatation balloon 14 that is mounted to the distal region of the shaft. Reference is made to the aforementioned Leary Patent 4,545,390 for further description of the type of catheter, the Leary patent being incorporated by reference herein. By way of example, the catheter shaft 12 may be of the order of 150 cm long and of the order of 0.50" diameter. The balloon may vary in size from about 1.5 mm to 4.5 mm diameter, for coronary use. The balloon may be considered as having a constant diameter cylindrical midportion 14M which expands to the nominal diameter, a pair of end cones 14C at the ends of the midsection 14M and a pair of neck sections 14N that extend outwardly from the narrow ends of the cones 14C. The balloon 14 is attached to the catheter shaft 12 by adhesively bonding the necks 14N to the catheter shaft 12.

Figure 4:
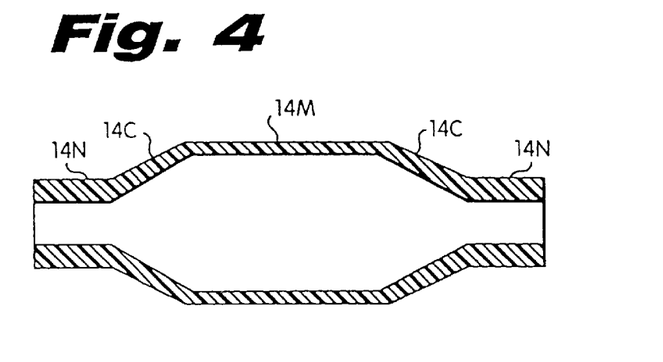
FIG. 4 is an enlarged diagrammatic cross-sectional illustration of a conventional balloon in which the thicknesses of the balloon material are highly exaggerated to illustrate the relative thicknesses of the balloon at the central cylindrical portion, the cone portion and the neck portion.
Figure 6:
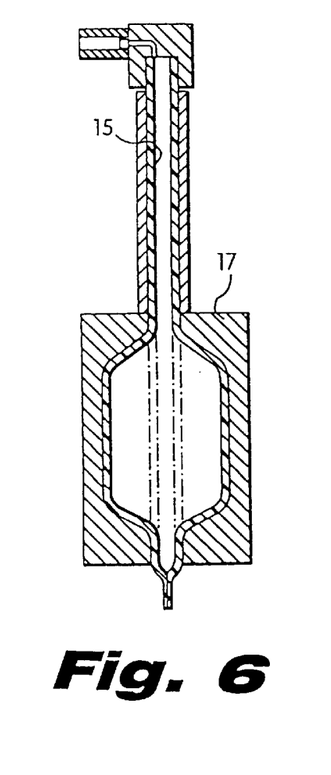
FIG. 6 is an illustration of the mold process used in making the balloon.

FIG. 4 shows a conventional balloon formed in one-piece, shown with its wall thicknesses exaggerated for ease of illustration. Such a balloon may be made according to the procedure described in U.S. Pat. No. 4,490,421 and U.S. patent application Ser. No. 001,759, filed Jan. 9, 1987, the disclosures of which are hereby incorporated by reference. The balloon is formed in a biaxially stretching process that includes blow molding in a mold of the type illustrated in FIG. 6. As described in further detail in the Levy patent, which is incorporated herein by reference, a tubular parison 15 of uniform inner and outer diameters and wall thickness is extended through the mold 17. The tubular parison is stretched axially and is blow molded radially within the mold 17. The portion of the tube 15 that forms the cylindrical midportion 14M is subjected to a greater degree of radial stretching than the neck portions 14N. Consequently, the midportion 14M will have less wall thickness than the neck portion 14N. The cones 14C are radially stretched to progressively varying degree as the diameter of the cones change. Thus, as illustrated in FIG. 4 the midportion 14M will have the thinnest wall, the neck 14N will have the thickest wall and the cones 14C will have a progressively increasing wall thickness in a direction extending from the ends of the midportion 14M to the necks 14N. The cones 14C and necks 14N thus are thicker than required. The increased thickness in the cones adversely affects the ability of the balloon to contract to a low profile. The greater thickness of the cones and the necks detracts from the trackability of the catheter.

Figure 5:
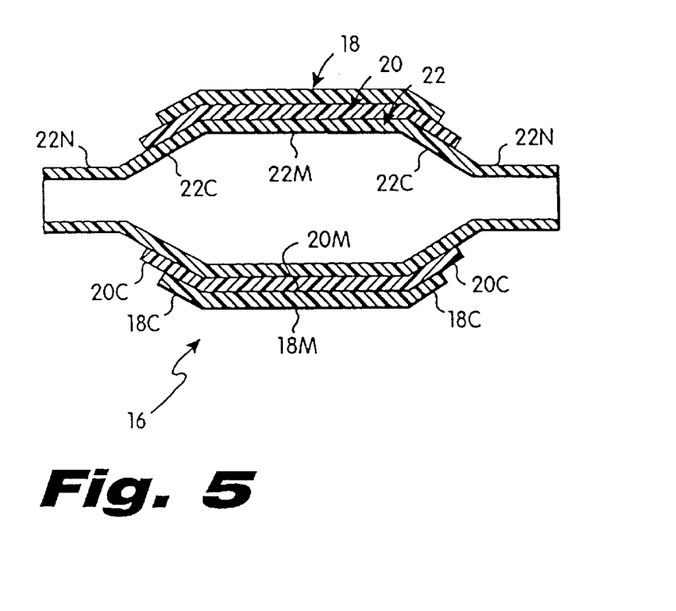
FIG. 5 is an enlarged diagrammatic cross-sectional illustration of a balloon made in accordance with the present invention.
Figure 7A:
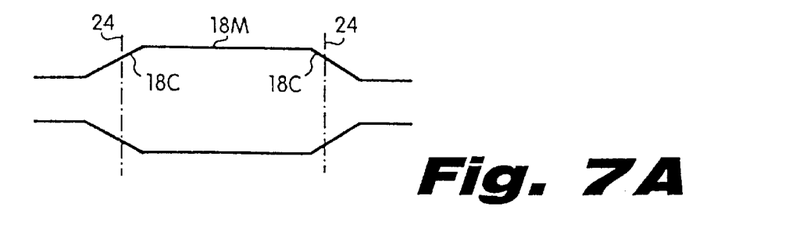
FIGS. 7A–7E are diagrammatic illustrations of the mold and the sequence of steps for making the balloon of the present invention.
Figure 7B:
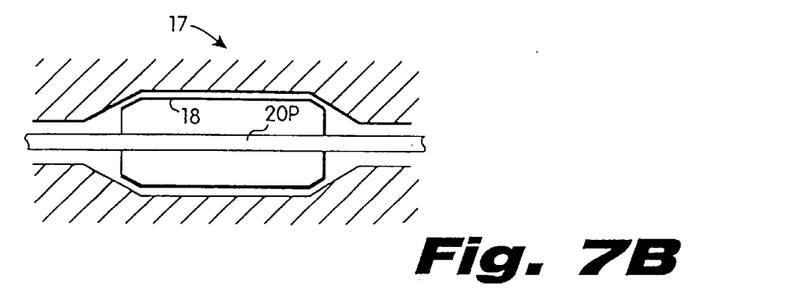
Figure 7C:
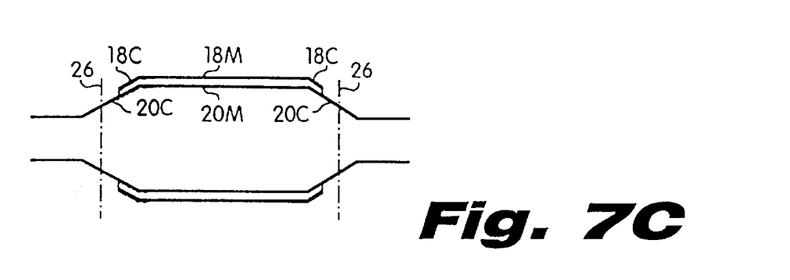
Figure 7D:
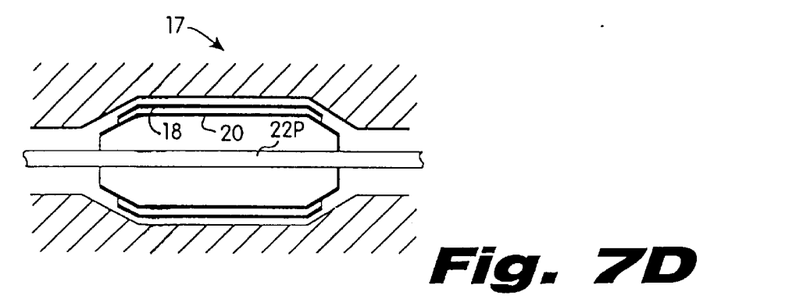
Figure 7E:
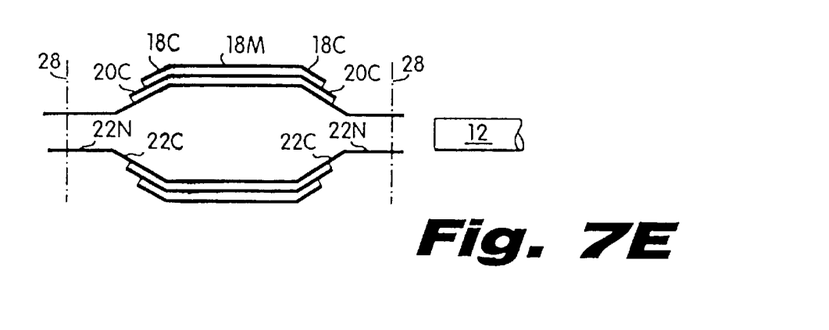

In accordance with the present invention, the balloon is formed from a plurality of relatively thin layers rather than a single unitary relatively thick layer. The configuration of a balloon made in accordance with the invention is shown in FIG. 5 in highly diagrammatic enlarged and exaggerated form. The illustrated balloon, indicated generally at 16, is formed from three layers including an outer layer 18, an intermediate layer 20 and an inner layer 22. The layers 18, 20, 22 are each in continuous intimate contact with each other and need not be adhesively attached. The balloon 16 is formed in a procedure illustrated diagrammatically in FIGS. 7A–7E. The mold 17, described in further detail in the Levy patent, receives a tubular parison 15 of the polymer from which the balloon is to be formed. The parison is relatively thin walled. The parison is stretched and expanded biaxially by combined axial stretching and blow molding as described in the Levy patent, to form a balloon having cones and neck extensions. In accordance with the invention, a first such balloon 18 is formed and is heat set at an elevated temperature as described in said application Ser. No. 001,759 and is then removed from the mold. The first balloon then is trimmed at each end between the ends of its cones as suggested at 24 in FIG. 7A, thus leaving a balloon midportion 18M and a pair of partial cones 18C. The first balloon, thus trimmed, then is replaced in the mold. A second elongate tubular parison 20P then is inserted into the mold as suggested in FIG. 7B and it is biaxially stretched and expanded. When the second parison 20P expands, it contacts fully and intimately the inner surface of the outer layer 18 contained within the mold. The second balloon thus formed also is heat set. After the intermediate balloon 20 has been formed, the combined outer and intermediate balloons 18, 20 are removed from the mold. The ends of the intermediate balloon layer 20 then are trimmed as suggested at 26 in FIG. 7C so that the intermediate cones 20C extend slightly outwardly of the shorter outer cones 18C. The two layer, partially formed balloon then may be reinserted into the mold and the process repeated with a third parison 22P of polymeric material as suggested in FIG. 7D. When the third layer 22 has been formed, the assembly of layers is again removed from the mold. The ends of the inner layer 22 then may be trimmed as suggested at 28 in FIG. 7E to leave the necks 22N and an exposed portion of the cones 22C. The balloon thus formed may be attached to the catheter shaft 12 by adhesively bonding the necks 22N to the catheter shaft.

It will be appreciated from the foregoing that the neck of the multiluminal balloon which is formed from an initial thin parison, although not expanded as much as the balloon midportion still is substantially thinner than the corresponding neck in a balloon formed in one-piece in a single layer. The regions of the cones similarly define a series of stepped thickness in which the thickness of the cone decreases in a direction extending away from the balloon midportion. Thus, although the cone segment in each of the three layers will tend to have increased thickness in an outward direction, the stepped down configuration of the cones, considered together, results overall in a cone thickness that is relatively small. For example, even in a thin wall high strength balloon made in accordance with the procedure described in application Ser. No. 001,759, the wall thickness in the cone ranges from about 0.0003" at its juncture with the cylindrical midportion to approximately 0.001" at its juncture with the neck. The neck portion may be of the order of 0.001".

By way of example, balloons made in accordance with the present invention may be formed from a tubular parison of polyethylene terephthalate having an inner diameter of the order of 0.0168" inner diameter and a wall thickness of the order of 0.0022". The parison is biaxially stretched about 3X in an axial direction and radially about 7X inner diameter stretch and about 5.5X outer diameter stretch. The resulting balloon will have a wall thickness in the cylindrical midportion region of the order of 0.0001", a cone thickness gradually increases from 0.0001" to about 0.0004" where the cone joins the neck and a neck portion having a wall thickness of the order of 0.0004". The aggregate wall thickness in the cylindrical midportion of the multiple layers is of the order of 0.0003" which is comparable to currently commercially available balloons. From the foregoing, it will be appreciated that the invention provides a new balloon dilatation catheter comprising an elongate, flexible shaft having a dilatation balloon mounted at the distal end. The balloon is formed from polymeric material and having a cylindrical midportion, an outwardly tapering conical portion at each end of the midportion and a cylindrical neck portion at the ends of the conical portions. The balloon is formed in at least two layers including an inner and outer layer, one of which is shortened and terminates in the region of the cones of the other, the necks of the balloon being adhesively attached to the shaft.

From the foregoing, it will be appreciated that the invention provides a new construction for a dilatation balloon, a new method for its manufacture and a new resulting catheter that will display improved characteristics as to trackability and reduced profile. It should be understood, however, that the foregoing description of the invention is intended merely to be illustrative thereof and that other embodiments, modifications and equivalents may be apparent to those skilled in the art without departing from its spirit.

Having thus described the invention, what I desire to claim and secure by Letters Patent is:

1. A multilayer balloon for a dilatation catheter, the interior of said balloon being in fluid communication with an inflation lumen within the dilatation catheter when mounted on said dilatation catheter, said multilayer inelastic balloon comprising at least a first and second layer of inelastic polymeric material layered one inside another, the length of said second layer being longer than the length of said first layer, wherein said layers are in continuous intimate contact with each other.

2. The multilayer balloon as in claim 1, wherein at least one of said layers is biaxially oriented.

3. The multilayer balloon as in claim 1, wherein at least one of said layers is thermoplastic.

4. The multilayer balloon as in claim 1, wherein each of said layers is semicrystalline.

5. The multilayer balloon as in claim 1, wherein said at least two layers comprises three layers of polymeric material, said third layer being adjacent to and longer than said second layer.

6. The multilayer balloon as in claim 1, wherein:
said second layer has a cylindrical midportion, an outwardly tapering conical portion at each end of said midportion, and a cylindrical neck portion at the ends of said conical portions.

7. The multilayer balloon as in claim 6, wherein said first layer has first and second ends positioned between, and not extending over, said neck portions.

8. A balloon dilatation catheter comprising:
an elongate flexible shaft and an inelastic multilayer balloon being mounted to the distal end of said shaft;
said shaft having an inflation lumen therein and the interior of said balloon being in fluid communication with said inflation lumen; and
a multilayer inelastic balloon comprising at least two layers of inelastic polymeric material layered one inside another, said layers being in continuous, intimate contact with each other, the length of one of said layers being shorter than the length of another of said layers.

9. A method of formning a multilayer dilatation balloon for coupling to a dilatation catheter, said method comprising:

forming a first balloon layer; then forming a second balloon layer longer than said first balloon layer, while simultaneously layering said first balloon layer in continuous intimate contact with each other said second to form said multilayer dilatation balloon.

10. The method of forming a multilayer dilatation balloon as in claim 9, wherein forming at least one of said balloon layers comprises blow molding a parison to form said balloon layer.

11. The method of forming a multilayer dilatation balloon as in claim 9, further comprising forming a third balloon layer adjacent to and longer than said second layer and in continuous intimate contact with said second layer.

12. The method of forming a multilayer dilatation balloon as in claim 11, wherein forming at least two of said balloon layers comprises blow molding separate parisons to form said at least two balloon layers.

13. The method of forming a multilayer dilatation balloon as in claim 12, wherein said blow molding further comprises sequentially blow molding first and second parisons to form respective first and second balloon layers of said multilayer dilatation balloon.

14. The method of claim 12, wherein each said layer is formed separately such that layering is sequential.

15. The method of forming a multilayer dilatation balloon as in claim 9, further comprising the steps of:

(a) blow molding one balloon layer in a mold to form a dilatation balloon having a cylindrical midportion, cones extending from the ends of the midportions, and necks extending from the ends of said cones;

(b) removing said one balloon layer from the mold and trimming its ends in the region of said cones;

(c) placing the trimmed balloon layer in the mold and then blow molding another balloon layer into intimate contact with the trimmed balloon;

(d) removing the assembly of balloon layers from the mold; and (e) trimming the ends of the last blow molded balloon layer to define the neck portion of the balloon.

16. The method for making a dilatation balloon as in claim 15, and further including repeating steps (c) and (d) after trimming the ends of the last blow molded balloon layer in the region of the cones and prior to step (e).

17. The method for making a dilatation balloon as in claim 15, and further including heat setting each balloon layer after the step of blow molding at a temperature greater than the blow molding step temperature.

18. The method for making a dilatation balloon as in claim 15, wherein each balloon layer is stretched throughout the blow molding step to thereby biaxially orient each balloon layer.

19. The method for making a dilatation balloon as in claim 18, and further including heat setting each stretched balloon layer at a temperature greater than the blow molding step temperature.

20. The method of claim 15 wherein each said layer is formed separately such that said layering is sequential.

* * * * *

UNITED STATES PATENT AND TRADEMARK OFFICE
CERTIFICATE OF CORRECTION

PATENT NO. : 6,004,289
DATED : December 21, 1999
INVENTOR(S) : Mark A. Saab

It is certified that error appears in the above-identified patent and that said Letters Patent is hereby corrected as shown below:

In column 3, line 45, delete first occurrence of "is".

In column 4, line 53, delete "thar" and insert -- than-- therefor.

In column 5, line 2, delete "-" after "to".

In column 6, line 15, delete "0.11711""and insert -- 0.117"-- therefor.

In column 6, Table 2, delete heading "Relative Stiffness ($t^3$)" and insert -- Relative Stiffness ($T^3$)-- therefor.

In column 7, line 2, delete "50%" and insert --5%-- therefor.

In column 7, line 54, delete "91.200" and insert --91,200-- therefor.

In column 8, line 22, delete "0.50"" and insert --0.50 cm-- therefor.

In column 10, line 65, delete "formning" and insert --forming-- therefor.

In column 11, lines 4-5, delete "each other".

In column 11, line 5, after "second" insert --balloon layer--.

Signed and Sealed this

Twenty-third Day of January, 2001

Attest:

*Attesting Officer*

Q. TODD DICKINSON
*Commissioner of Patents and Trademarks*